United States Patent [19]

Berger

[11] Patent Number: 5,804,701
[45] Date of Patent: Sep. 8, 1998

[54] COMPACT, LOW-PROFILE CHROMATOGRAPH

[75] Inventor: Terry A. Berger, Newark, Del.

[73] Assignee: Hewlett-Packard Company, Palo Alto, Calif.

[21] Appl. No.: 731,943

[22] Filed: Oct. 22, 1996

[51] Int. Cl.[6] ................................................. G01N 30/02
[52] U.S. Cl. .............................. 73/23.42; 96/105; 96/106
[58] Field of Search ................................. 73/23.39, 23.4, 73/23.41, 23.42, 23.35, 61.52, 61.53, 61.55, 61.56; 95/87, 85, 82; 96/101, 105, 106, 107; 422/89

[56] References Cited

U.S. PATENT DOCUMENTS

| | | | |
|---|---|---|---|
| 3,069,894 | 12/1962 | Claudy | 73/23.42 |
| 3,095,746 | 7/1963 | Reinecke et al. | 73/23.42 X |
| 3,213,883 | 10/1965 | Carls . | |
| 3,234,963 | 2/1966 | Lyon . | |
| 3,391,703 | 7/1968 | Kay . | |
| 3,538,744 | 11/1970 | Karasek . | |
| 3,916,465 | 11/1975 | Jones | 73/23.35 X |
| 3,996,017 | 12/1976 | Kaiser . | |
| 4,474,889 | 10/1984 | Terry et al. . | |
| 4,771,628 | 9/1988 | Sisti et al. | 73/23.39 X |
| 4,854,952 | 8/1989 | Stepien | 73/23.35 |
| 4,891,120 | 1/1990 | Sethi et al. . | |
| 4,905,497 | 3/1990 | Shindo et al. . | |
| 4,935,040 | 6/1990 | Goedert . | |
| 5,234,032 | 8/1993 | Kline et al. . | |
| 5,298,225 | 3/1994 | Higdon . | |
| 5,340,543 | 8/1994 | Annino et al. . | |
| 5,567,868 | 10/1996 | Craig et al. | 73/23.42 |

OTHER PUBLICATIONS

James. B. Angell, Stephen C. Terry and Phillip W. Barth, "Silicon Micromechanical Devices", Scientific American, Mar. 1983, pp. 44–55.

*Primary Examiner*—Michael Brock
*Attorney, Agent, or Firm*—Mark Z. Dudley

[57] ABSTRACT

An analytical instrument includes a control system, including a computer and a pneumatic controller responsive to the computer, and a planar chromatographic assembly. The planar chromatographic assembly includes a planar pneumatic manifold, a heater/fan assembly for establishing a temperature-controlled zone, an insulating enclosure for confining the temperature-controlled zone to an oven cavity and certain zones of the planar pneumatic manifold, a separation column having inlet and outlet ends attached to couplers at selected internal fluid-bearing conduits in the pneumatic manifold and located closely adjacent the planar manifold and within the temperature-controlled zone, and one or more fluid-handling functional devices attached to the pneumatic manifold for fluid-tight communication with respective internal etched channels provided within in the planar pneumatic manifold. The fluid-handling functional devices may be surface-mounted or edge-mounted to certain ones of the etched channels in the planar pneumatic manifold. The fluid-handling functional devices may include: a) passive devices such as an injector section, a fluid coupler, or a vent for coupling a fluid stream to or from a selected fluid-bearing conduit; b) active devices such as a valve, a fluid regulator, a fluid flow input device (fluid source), operable in response to a control signal from the control system for controlling fluid flow in one or more selected etched channels in the planar manifold, or c) signal generating devices such as a sensor or detector operable so as to provide sense or detection signal indicative of a characteristic of the fluid flow in an etched channel or in the separation column. The combination of the planar manifold and the edge- or surface-mounted fluid-handling functional devices allows the planar chromatographic assembly to be constructed in a compact, low-profile form factor.

9 Claims, 9 Drawing Sheets

COMPACT, LOW-PROFILE CHROMATOGRAPH

FIELD OF THE INVENTION

The present invention relates to an analytical instrument, and more particularly with a chromatographic assembly having a compact, low-profile form factor.

BACKGROUND OF THE INVENTION

Analytical instruments which rely upon regulated fluid flow are commonly employed in a wide variety of applications, such as sample purification, chemical analysis, clinical assay, and industrial processing. Gas and liquid chromatographs are particular examples of a fluid flow system wherein certain characteristics related to a particular fluid flow are detected, e.g., the presence or absence of a fluid component, such as an analyte or contaminant. For many chromatographs, an extensive and complex array of tubing, fittings and the like are employed to provide the many flow paths that are necessary for optimum operation, and by the attachment of differing, plural sensors. A practical problem remains of connecting the large number of valves, sensors, fittings, and the like that are required for the multitude of flow path combinations in a chromatograph. The complexity of such systems also introduces reliability concerns. Because the devices that are implemented in these flow systems are sometimes automated, the reliability and accessibility are features critical to successful instrument operation.

Another problem involves the proper orientation of all of the valves, sensors, and the like so as to allow the desired combinations of flow paths, yet also provide an assembly that is compact, easily-manufactured, inexpensive, and reliable. For example, the provision of fluid-tight connections in a complex fluid-handling assembly has become exceedingly problematic as the assembly is reduced in size. Some gas chromatographs employ fluids in the form of combustible gasses in performing an analysis. Even though the pneumatic fittings in the typical chromatograph are designed to minimize leakage, one may nonetheless consider a pneumatic fault mode wherein a gas leak could occur and sufficient gas could accumulate so as to pose an unsafe condition.

It will also be appreciated that a flow system in a gas chromatograph must be versatile, that is, capable of being reconfigured during an instance of repair or modification, or to meet the requirements of a particular application as additional valves, fittings, etc. are added to the flow system.

The conventional gas chromatograph is accordingly too large and bulky for many applications that could otherwise benefit from chromatographic analysis. The conventional gas chromatograph is difficult to build and requires a complex array of expensive materials and parts that are specialized (non-standard or low volume parts) such that their manufacture is labor-and capital-extensive. Due to its power requirements and its inefficient power usage, the conventional gas chromatograph consumes much power and typically requires a temperature-controlled environment if operated in a confined space.

For example, there is a need in many chemical processing plants for a gas chromatograph that can be located in a somewhat harsh environment and dedicated to monitoring the concentration of components in a specific chemical processing stream. Such devices are called process Gas chromatograph's. Process gas chromatograph's are currently constructed and implemented by use of a laboratory-grade gas chromatograph that has been repackaged (e.g. "ruggedized"). The devices are large, unwieldy, and expensive. There is a need for a portable gas chromatograph that exhibits many of the characteristics desirable in a process gas chromatograph. These include: simplicity, robustness, ease of use, minimal maintenance, and low cost.

Recent attempts at providing a miniaturized gas chromatograph have generally followed one of three design approaches.

A first approach is to construct some of the conventional gas chromatograph components in miniature form using conventional materials and techniques, thus affording a minor reduction in the overall size and format of the gas chromatograph when assembled. Exemplary patents in the area include U.S. Pat. No. 3,996,017 (Kaiser); 5,298,225 (Higdon); and 5,340,543 (Annino et al.) Unfortunately, this approach has not produced a truly low-cost, reliable, and compact gas chromatograph. Such miniaturization typically increases the manufacturing cost and complexity of the miniaturized components, and assembly of such components into a complete system is difficult and often requires automated assembly line.

Another, widely-divergent approach utilizes techniques developed in the arts of semiconductor fabrication and micro-electro-mechanical systems (MEMS) to radically reduce the size and format of the gas chromatograph. The success of this approach is dependent upon micro machining all of the components of a gas chromatograph in a silicon or semiconductor chip; exemplary patents are U.S. Pat. Nos. 4,905,497 (Shindo); 4,935,040 (Goedert), and in Angell et al., "Silicon Micromechanical Devices", *Scientific American*, March, 1983. This approach is still in a nascent phase and has been fraught with high design and manufacturing costs, low yields, and intractable performance and reliability problems. For example, the materials necessary for fabrication of a micromachined gas chromatograph-on-a chip are only partially compatible with the operating modes of a full function gas chromatograph. Components need to be robust (not brittle), inert, and compatible with high temperatures and rapid temperature changes. Micro machining also tends to produce devices so small that they can be ill-suited for manual operation, such as in the step of injecting a sample via an syringe needle into a micromachined separation column.

Still another, intermediate approach is to employ micro machining techniques for constructing only one or two of the components, which are then employed in a system based on the conventional laboratory gas chromatograph; exemplary patents include U.S. Pat. Nos. 3,538,744 (Karasek) and 4,474,889 (Terry et al.) However, this approach seems to retain many of the disadvantages of each of the prior two approaches, and does not offer much countervailing improvement in reducing the cost, complexity, and size of the gas chromatograph.

SUMMARY OF THE INVENTION

The advantages of the invention are achieved in a planar chromatographic assembly suitable for use as with a control system so as to provide an analytical instrument. The planar chromatographic assembly includes a planar pneumatic manifold, a heater/fan assembly for establishing a temperature-controlled zone, an insulating enclosure for confining the temperature-controlled zone to a side of the planar pneumatic manifold, an injector section, a separation column having inlet and outlet ends attached to selected internal fluid-bearing conduits in the pneumatic manifold and which is located within the temperature-controlled zone, and one or more fluid-handling functional devices attached to the pneumatic manifold for fluid-tight communication with respective internal etched channels provided within in the planar pneumatic manifold. The fluid-handling functional devices may be surface-mounted or edge-mounted to certain ones of the etched channels in the planar pneumatic manifold. The fluid-handling functional devices may include: a) passive devices such as a fluid coupler or a vent for coupling a fluid stream to or from a selected fluid-bearing conduit; b) active devices such as a valve, a fluid regulator, or a fluid flow input device (connectable to a fluid source) operable in response to a control signal from the control system for controlling fluid flow in one or more selected etched channels in the planar manifold, or c) signal generating devices such as a sensor or detector operable so as to provide sense or detection signal indicative of a characteristic of the fluid flow in an etched channel or in the separation column.

In a first aspect of the present invention, the planar chromatographic assembly is provided in a compact, low-profile form factor thus enabling its use as a portable unit, or for easy attachment in a confined space with respect to a flow system to be analyzed, thus enabling an analysis of a chemical process in an "on-line", "at-line", or similarly oriented type of chemical process analysis.

In another aspect of the present invention, the planar chromatographic assembly is enclosed in an insulating enclosure for operation in an adverse environment.

In another aspect of the present invention, the planar chromatographic assembly is constructed with use of a planar pneumatic manifold for effecting fluid connections and fluid handling functions in a very small volume while offering excellent reliability and long life.

In another aspect of the present invention, the planar chromatographic assembly utilizes miniaturized fluid handling functional devices and a planar manifold having a very small heated zone so as to conserve heat, consume little power, and thus be energy-efficient.

In another aspect of the present invention, the planar chromatographic assembly utilizes a conventional separation column for ease of use, cost savings, and versatility.

DETAILED DESCRIPTION OF THE PREFERRED EMBODIMENT

The present invention will find useful application in a variety of analytical systems that benefit from analysis of one or more fluid streams.

Certain apparatus and methods of the present invention may be employed in particular to provide initiation, distribution, redirection, termination, control, sensing, and other types of functions (collectively defined herein as fluid-handling functions) with respect to one or more of such fluid streams. Gases are the preferred fluids according to the practice of the present invention, and therefore the following description of the invention will include a description of the arrangement, construction, and operation of certain pneumatic devices, and hence is particularly directed to the control and analysis of a gaseous stream in a gas chromatographic analytical system (hereinafter, a chromatograph). However, for the purposes of the following description, the term "pneumatic" will also be considered to refer to all types of fluids.

It should be understood that the teachings herein are applicable to other analytical instruments, including liquid chromatographs, high-pressure gas chromatographs (HPGC), high pressure liquid chromatographs (HPLC), supercritical fluid chromatographs (SFC), and supercritical fluid extraction (SFE) instruments.

In the Figures and the description to follow, like nomenclature and numeric identifiers will refer to like components; signal lines are drawn schematically by single solid lines; pneumatic flow lines or channels are drawn schematically as double solid lines; and components, lines, or channels in phantom are schematically drawn in dashed lines.

Figure 1:
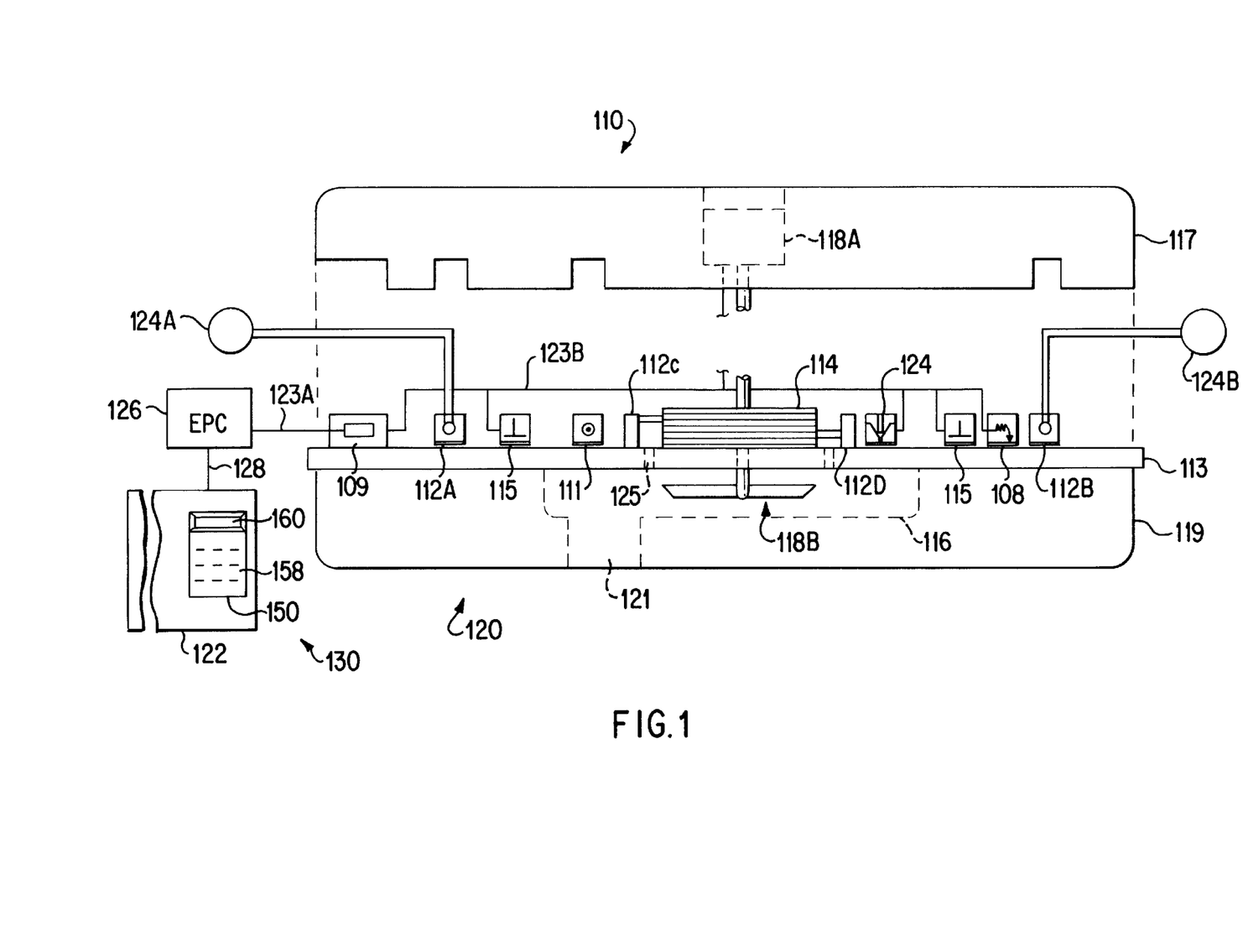
FIG. 1 is a simplified block diagram of chromatograph constructed to include a planar chromatographic assembly in accordance with the present invention.

A new and novel analytical instrument is shown in FIG. 1 and is generally designated chromatograph 110 having a planar chromatographic assembly 120 and a control section 130. The planar chromatographic assembly 120 is provided in a compact, low-profile form factor such that, in comparison to a conventional gas chromatograph, the planar chromatographic assembly 120 occupies less volume, has a smaller footprint, is amenable to configuration as a portable unit, is less complex and costly to manufacture, and consumes less operating power. For the purposes of this description, "compact" refers to a characteristic of the planar chromatographic assembly that allows its implementation in a package that fills a very small volume, on the order of 3000 to 5000 cubic centimeters. "Low-profile" and "low-profile form-factor" refers to an overall profile or aspect ratio of the planar chromatographic assembly that allows its implementation in a package that is generally planar, having a thickness on the order of 6 to 10 centimeters, a width up to 18 to 24 centimeters, and a length up to 28 to 34 centimeters.

Hence, the size and shape of the contemplated planar chromatographic assembly may be likened to what is currently known as a notebook portable computer, (or preferably smaller) such as the Omnibook line of portable computers manufactured by Hewlett-Packard Company, Palo Alto, Calif.

In order to perform a chromatographic separation of a given sample compound, a sample is injected into the planar chromatographic assembly 120 with a pressurized carrier gas by means of a sample inlet 111. The carrier gas supplied to inlet 111 is provided from a source 124A through one or more fluid couplers 112A into a planar pneumatic manifold (hereinafter, planar manifold) 113, which incorporates internal conduits capable of bearing fluid flow, hereinafter termed channels, each of which serve in part to control and redirect a plurality of gas flows, including the carrier gas and a plurality of detector gases of appropriate types, such as air, hydrogen, and make-up gas. The detector gases are provided from respective sources (one such source 112B is shown) through respective couplers 124B to the planar manifold 113. A separation column 114 is positioned within an oven cavity 116 defined by the planar manifold 113 on one side and a lower insulating enclosure 117 on the other. The lower insulating enclosure 117 serves to insulates the oven cavity from the ambient environment. An upper insulating enclosure 119 is fitted so as to insulate the other side of the planar manifold 113, and is notched to allow edge mounting of some or all of the aforementioned fluid-handling functional devices. The separation column 114 is connected at its inlet and outlet ends to selected channels in the planar manifold 113 by respective couplers 112C, 112D. The carrier gas/sample combination passing through column 114 is exposed to a temperature profile resulting in part from the operation of a heater/fan assembly 118A, 118B which directs ambient air through vents 121 and/or ports 125 to and from oven cavity 116. During this profile of changing temperatures, the sample will separate into its components primarily due to differences in the interaction of each component with the column 114 at a given temperature. As the separated components exit the column 114, they are detected by a detector 124.

In a first feature of the present invention, the fluid-handling functional devices integrated in the planar chromatographic assembly 120 are contemplated as being edge-mounted or surface-mounted to the planar manifold 113. Whether they are edge-mounted or surface-mounted depends on the particular application of the present invention, however (and as shown in FIG. 1) it is advantageous to locate certain ones of the devices at one edge of the planar manifold 113 for accessibility. The contemplated fluid-handling functional devices include passive devices such as the aforementioned inlet 111 and couplers 112A, 112B, 112C, 112D; active devices such as valves 115 or regulators (not shown in FIG. 1); and signal generating devices such as sensors 108, detector 124, and the like.

Figure 4A:
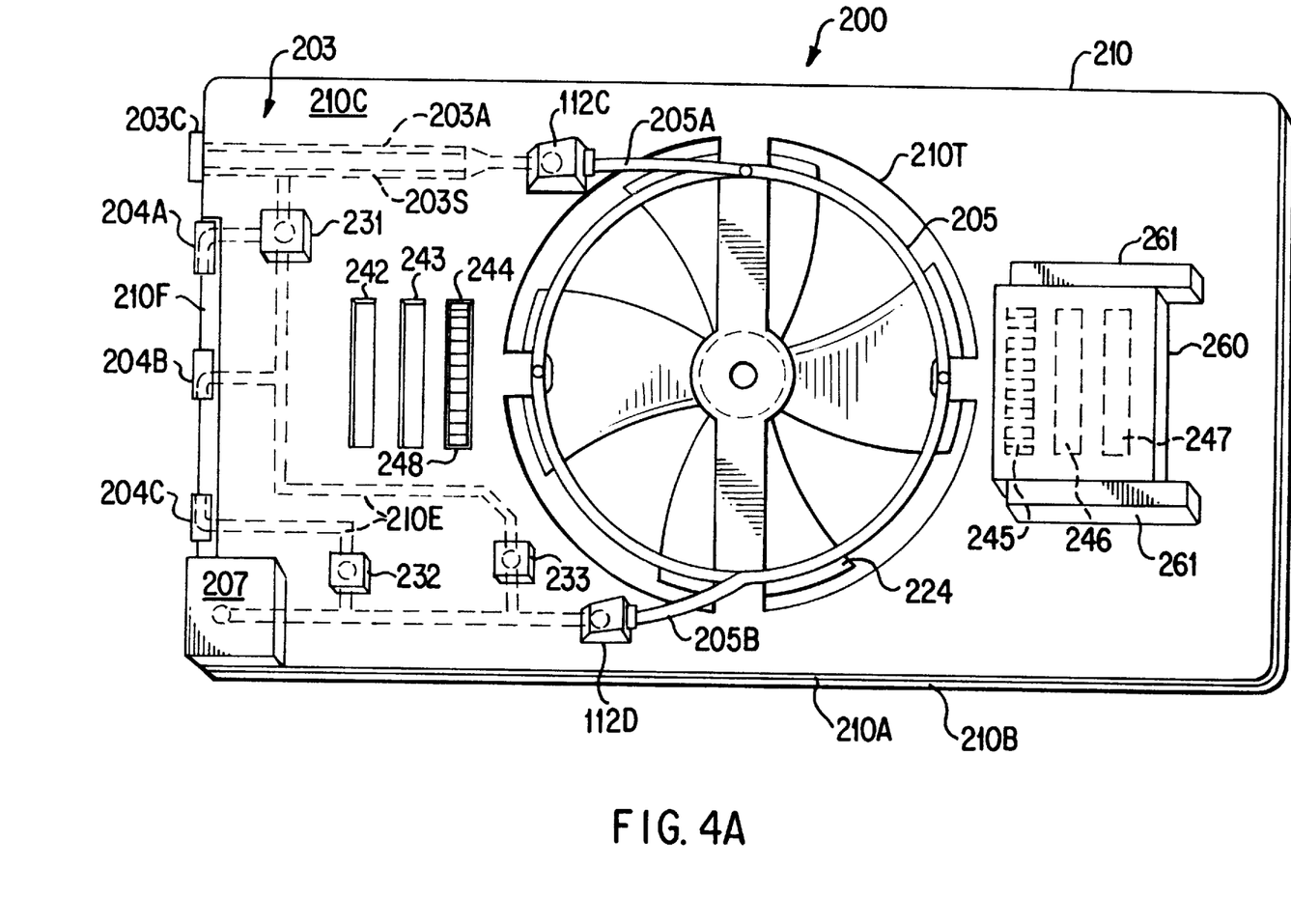
FIG. 4A is an elevated perspective view of the planar chromatographic assembly preferred for use in the chromatograph of FIG. 2, with certain components of the planar chromatographic assembly being omitted for clarity.

Among the various fluid-handling functional devices, the active devices and the signal generating devices are contemplated as being operated under control signals generated by the control section 130 on data and control lines 123A, 123B, and 128 connected to computer 122 and pneumatic controller 126. For example, the pneumatic controller 126 effects control of, among other things, the characteristics of the fluid flows in the planar manifold 113, such as fluid flow rate, fluid pressure, fluid flow regulation, and the continuity or discontinuity of flow. As further example, the time during which a particular valve 115 on the planar manifold 113 will remain open and closed in relation to control signals received on the data and control line 128 and in accordance with certain operating conditions of the chromatograph 110. Control and data line 123A allows the return of sense information from appropriate signal-interface electronics in active and signal generating devices (the valves 115, detector 124 etc.). Accordingly, the computer 122, pneumatic controller 126, and planar manifold 113 may be operated to effect a variety of fluid handling functions. The controller 126 and computer 122 are shown as a distinct blocks for clarity, but it will be recognized that their functions may be performed by an electronic module integrated in the planar chromatographic assembly 120. Also, the programming associated with computer 122 that is utilized in relation to the present invention will be readily understood from the description herein. The planar manifold assembly 110 preferably includes one or more edge- or surface-mounted connectors 109 and associated cabling (shown in simplified form as line 123B for clarity) for control, data, and power signals as may be needed for operation of the detector 124, valves 115, sensors 108, fan motor 118A, linear motors 261 (FIG. 4), and the like.

Computer 122 maintains overall control of all systems associated with the chromatographic assembly 120. By monitoring the operation of the chromatograph 110 by signals from certain components, such as the detector 124, the computer 122 can initiate and maintain certain functions required for an analytical run. The computer 122 includes a central processing unit and all associated peripheral devices, such as random access memories, read-only memories, input/output isolation devices, clocks and other related electronic components. In the preferred embodiment, the central processor used in computer 122 is a microprocessor. As such, computer 122 includes a memory in which information and programming can be stored and retrieved by known methods. However, it will be appreciated that the programmed control of pneumatic controller 126 can be implemented by other computing means, such as an embedded microprocessor or discrete controller circuit integrated into in the chromatographic assembly 120. It is contemplated that for some applications an optional interface in the form of an electronic control panel 150 having a keypad 158 and a display 160 may be included. Consequently, indicating or prompt messages can be generated by computer 122 and displayed on display 160. Operating commands and other information may be entered into computer 122 by way of keypad 158.

Figure 2A:
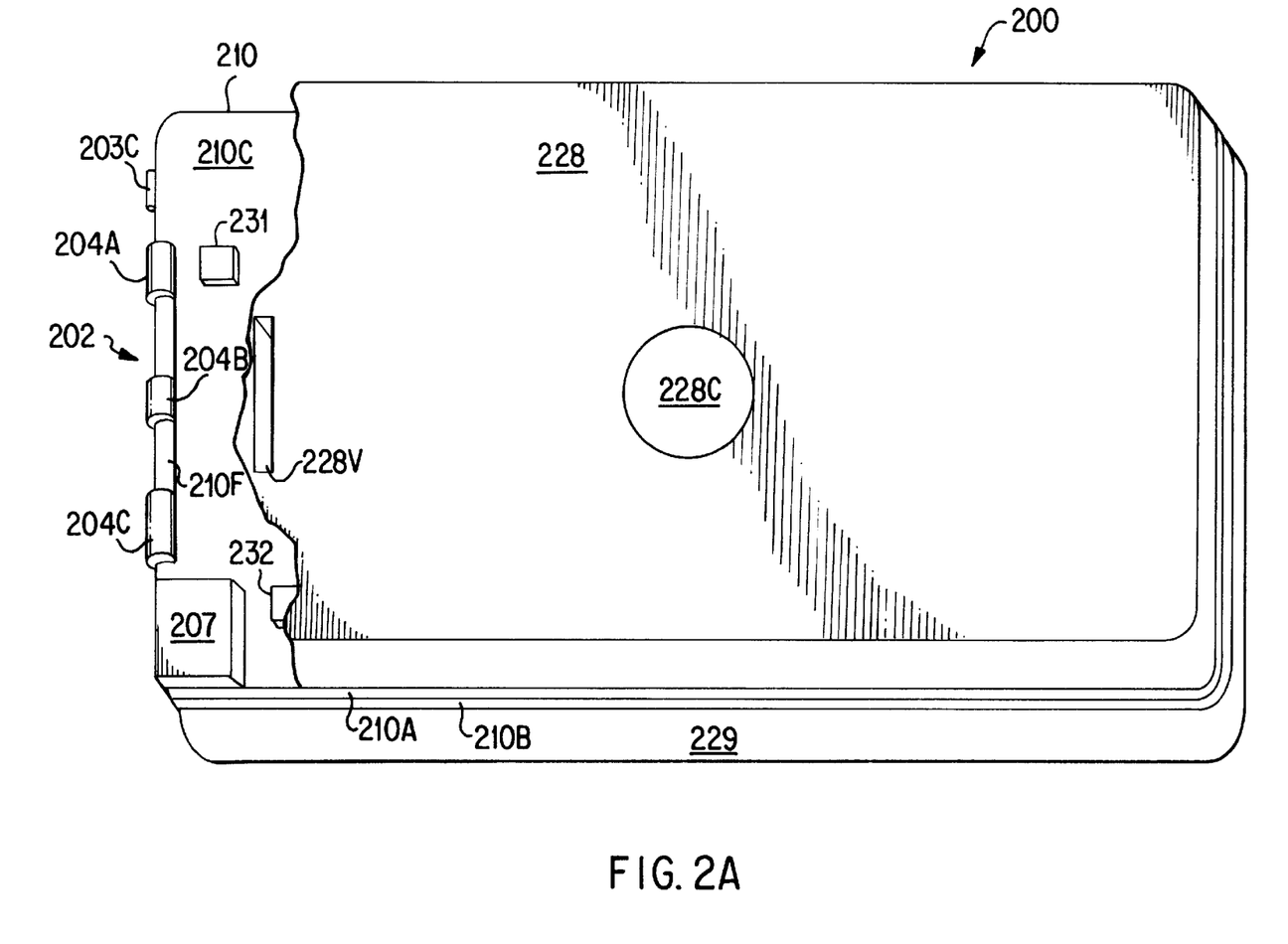
FIG. 2A is a side perspective view of preferred embodiment of a planar chromatographic assembly in the chromatograph of FIG. 1.
Figure 2B:
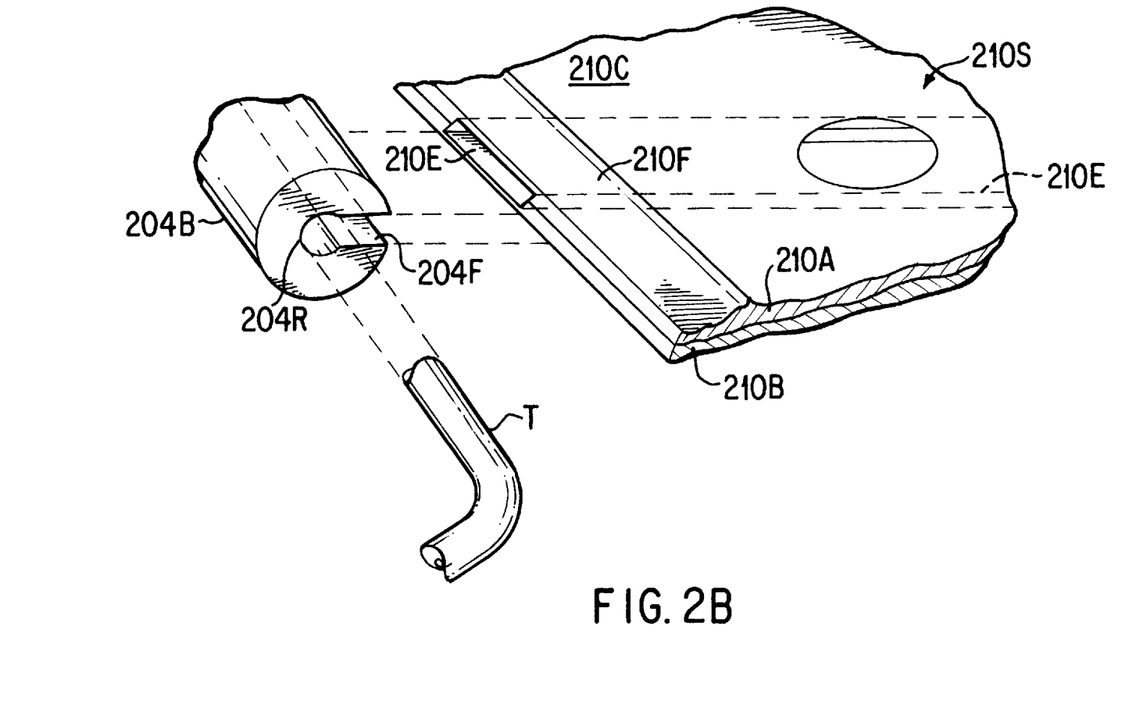
FIG. 2B is side perspective view of a portion of the planar chromatographic assembly of FIG. 2A, illustrating an embodiment of an edge-mounted fluid-handling functional device in exploded view for clarity.
Figure 3A:
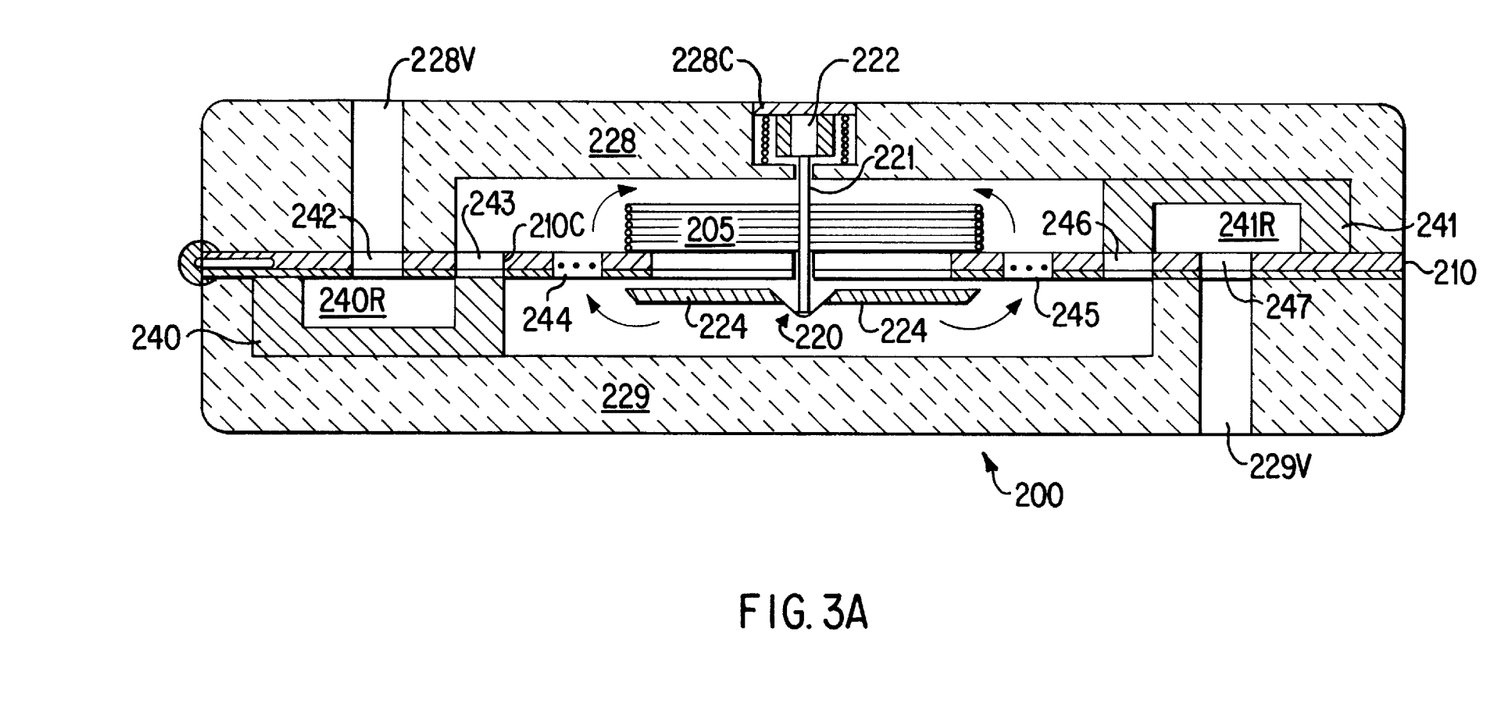
FIGS. 3A and 3B are side sectional views of a preferred embodiment of the planar chromatographic assembly operable in the chromatograph of FIG. 2.
Figure 3B:
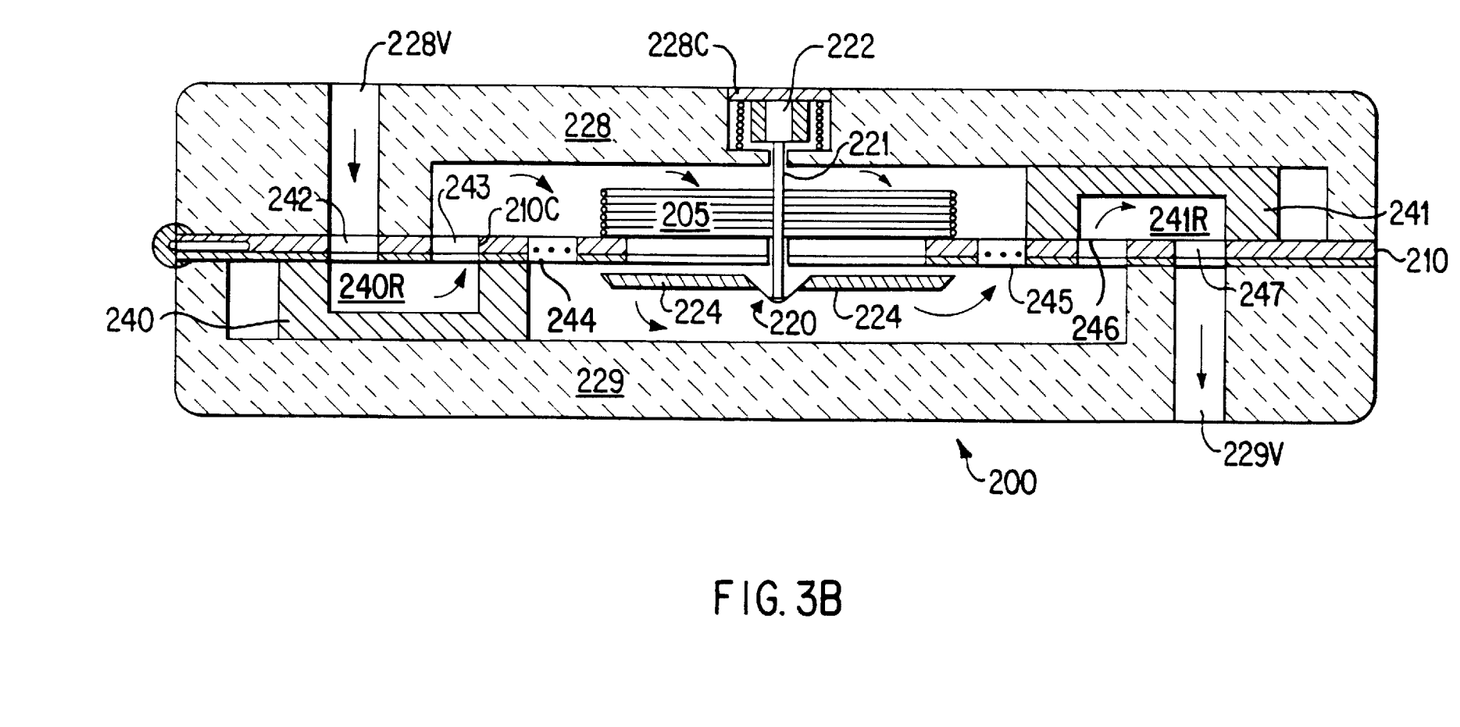
Figure 4B:
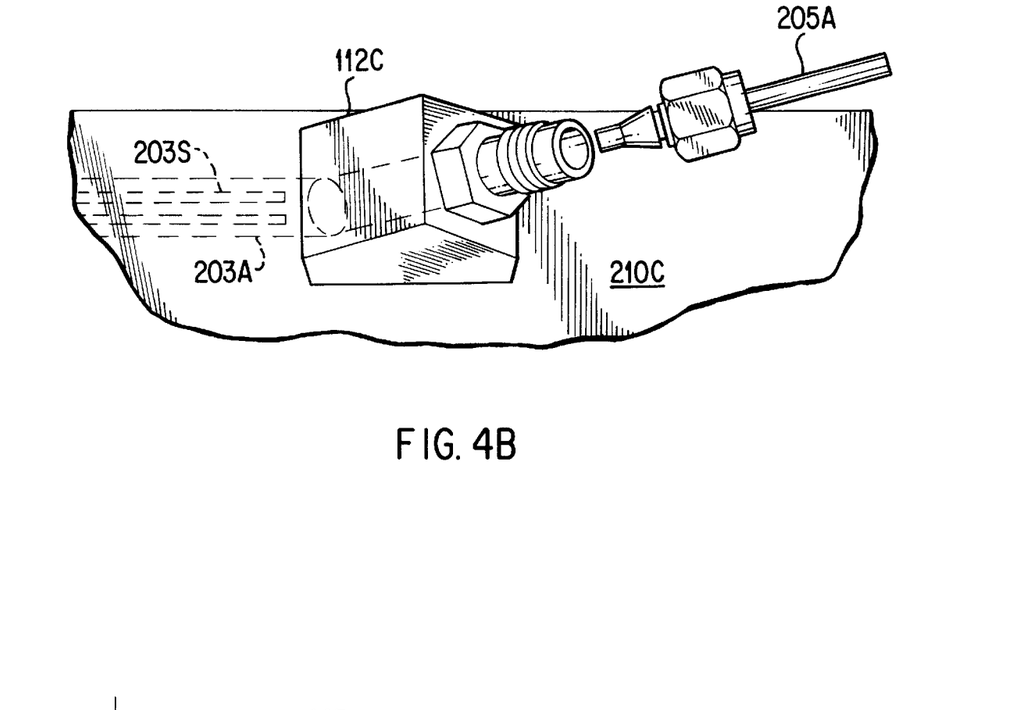
FIG. 4B is an elevated perspective view of a coupler preferred for use in attaching the inlet end of a separation column to a planar manifold in the planar chromatographic assembly of FIG. 2, with certain components of the planar chromatographic assembly being omitted for clarity.
Figure 4C:
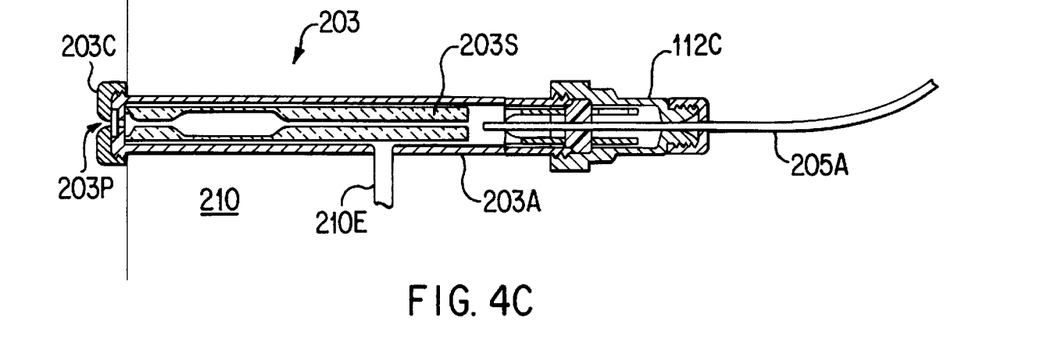
FIG. 4C is a simplified cross-sectional view of the coupler of FIG. 4B and an inlet section integrated into an edge portion of the planar chromatographic assembly of FIG. 2, with certain components of the planar chromatographic assembly being omitted for clarity.

FIGS. 2–4 illustrate a preferred embodiment 200 of the planar chromatographic assembly 120 of FIG. 1. In the preferred embodiment, the illustrated embodiment 200 includes a planar manifold 210 having a pneumatics section 202 including associated fluid-handling functional devices that are edge-mounted or surface-mounted to the planar manifold 210. An insulating enclosure is provided as two removable covers 228, 229 each preferably attachable to the respective perimeters of the upper and lower major surfaces 210C, 210D of the planar manifold 210 for insulating the planar manifold 101, and some or all the fluid-handling functional devices mounted thereon, from ambient conditions. The preferred embodiment 200 thus includes the planar manifold 210 comprising front plate 210A and back plate 210B having respectively exposed upper and lower major surfaces 210C, 210D; a fan 220 having fan shaft 221, fan motor 222, and fan blades 224; a flow-through opening 210T in the planar manifold 210 permitting the exchange of air by operation of the fan 220 between the upper and lower major surfaces 210C, 210D; an inlet section 203 integrated into an edge portion of the planar manifold 210, having an inlet septum cap 203C, inlet channel 203A, and inlet liner 203S; fluid line couplers 204A, 204B, 204C; a separation column 205 having inlet end 205A and outlet end 205B; a detector section 207; a column cover 228 and a fan motor cap/heat sink 228C located in the column-side cover 228; and an oven cavity cover 229. Mounted to the planar manifold 210 are a first valve 231, a second valve 232, a third valve 233 a shutter assembly including, an intake shutter 240 having a recess 240R, an exhaust shutter 241 having recess 241 R, and respective linear shutter motors (only one of which, linear motor 261 is illustrated for clarity). The intake shutter 240 is selectably positionable with respect to intake ports, 242, 243, 244 and the exhaust shutter 241 is selectably positionable with respect to exhaust ports 245, 246, 247 by the linear motors. Intake port 244 and exhaust port 245 each include a longitudinal heating element cartridge 248 that may be selectively actuated to heat the air passing therethrough.

In the preferred embodiment of the planar manifold 210 contemplated by the present invention, the front plate 210A and a back plate 210B may be seen to be sized and constructed to be superimposed and bonded together during the manufacturing process to form the planar manifold 210. Preferably, the front plate 210A and back plate 210B are machined from stainless steel and etched to provide an arrangement of etched channels 210E each capable of sustaining fluid flow. That is, the etched channels 210E form a predetermined array of internal conduits when the front plate 210A and back plate 210B are bonded together to form the planar manifold 210. The preferred method of bonding is diffusion bonding, which generally is known in the art and is described in, for example, U.S. Pat. No. 3,530,568, the disclosure of which is included herein by reference. However, in other embodiments, other materials and bonding methods may be employed, and a number of intermediary plates (such as one, two, or more, not shown) are also contemplated being provided intermediate the front plate 210A and back plate 210B to form a multi-layer configuration. In contrast to the conventional approach, wherein the task of forming complex interconnected flow paths usually involves the use of many discrete pieces of tubing and a block-like manifold through which the pieces of tubing can be attached, the planar manifold 210 replaces conventional manifolds at a fraction of the cost and with minimal labor. Further details on the design and manufacturing of a planar manifold having etched channels therein may be found in commonly-assigned U.S. Pat. No. 5,567,868, issued to Craig et. al., the disclosure of which is included herein by reference.

The planar manifold 210 is robust, rigid, shock proof, and unaffected by operation in a high temperature environment. The contemplated planar manifold 210 can be drilled, bent, welded, etc. Hence, the planar manifold 210 is intended as the primary structural support member of the embodiment 200, in addition to serving as a pneumatic flow manifold for managing a complex arrangement of fluid flows.

It is contemplated that the etched channels in one or both of the front and back plates 210A, 210B may lack the appropriate geometry for certain flow paths necessary for operation of the planar chromatographic assembly 120. For optimum chromatography, the flow paths in contact with the sample preferably have a circular cross section and side walls that are chemically inert. A transverse section of the some portions of an etched channel 210E may be found to be rather shallow and possibly wider at the plate surface than at the deeper portion of the channel. In addition, the longitudinal edges of two superimposed channels may define, in some areas, a thin crevice that can act as a sample diffusion chamber. This channel geometry can produce undesirable band broadening.

The planar chromatographic assembly 120 in the present invention is constructed to address this problem in three ways. Firstly, it is contemplated that many of the etched channels in the planar manifold 210 are not employed to carry the sample flow and hence their cross sectional shape is more or less irrelevant. Secondly, rather than employ an etched channel in the planar manifold 210 as a separation column, the preferred embodiment 200 employs a conventional version of an open capillary column, such as a circular cross section, hollow, fused silica tubing or a metal tubular column, as the separation column 205. Thirdly, certain portions of the etched channels 210E that are likely to be in contact with the sample are preferably equipped with a discrete liner, such as a section of fused silica capillary tubing, or subject to diffusion coating of an inert material such as nickel fluoride. Such measures may be taken prior to assembly of the planar manifold 210 to enhance the inertness of selected channels and to improve the channel geometry. In particular, and as shown in FIG. 4C, the etched channel 203A in the vicinity of the injection port may be augmented with an injection port liner 203S in the form of piece of circular cross section, hollow, fused silica tubing that is positioned in the etched channel before the front and back plates 210A, 210B are joined.

In many applications, one gas supply may be used for several differing purposes within a single planar chromatographic assembly 120. For example, a single source of hydrogen may be supplied to an etched channel configured as a "tee" to split the hydrogen flow into two flow paths. Separate flow control devices (such as valves 231, 233) are then mounted to control certain etched channels so as to allow individual control of the gas flow in each etched channel. For example, such flow paths are used to transport air or make-up gas supplied from coupler 204A, carrier gas supplied from the coupler 204B, and detector gas supplied from coupler 204C to precisely the points in the planar manifold 210 where such gas flows are needed. In another example, in an injection port 203P in the inlet section 203, a small amount of carrier gas is used for split vent flow or as purge gas that is directed across the surface of a septum used to seal the inner portion of the inlet section 203 from the ambient environment. A septum purge prevents any compounds that may outgas from the septum from entering the separation column 205 and appearing to be either background noise or a sample component. For example, hydrogen might be used for the carrier gas, for the septum purge, and also as a fuel for a detector section 207 constructed in the form of a flame ionization detector (FID). Similarly, in a split injection, much of the carrier gas entering the inlet section 203 is vented through an etched channel that acts as a split vent using appropriate flow or pressure control hardware (not shown).

As shown in FIG. 2B, the etched channels 210E may be directed to a surface port 210S having an opening suitable for effecting fluid communication with a complementary port in a surface mounted fluid-handling functional device. Alternatively, the etched channels 210E may be directed to the edge of the planar manifold 210 (and preferably in the vicinity of the pneumatics section 202) where an interface surface 210F is located for receiving a plurality of edge-mounted fluid handling functional devices, such as the inlet section 203 and couplers 204A, 204B, and 204C. (Further description of the mounting and operation of suitable surface-mounted fluid handling functional devices will be described with reference to FIGS. 5 and 6).

Preferably, the edge-mounted fluid handling functional devices are constructed as generally cylindrical fitting having a slot machined along the major axis of the fitting such that the piece can frictionally engage the prepared interface surface 210F on the edge of the planar manifold 210. Sliding the slot over the manifold edge produces a tight fit between the interface surface 204F and the interface surface 210F on the edge of the planar manifold 210. A receiving bore 204R is provided to frictionally engage one end of a gas tubing T such that fluid communication is effected between the internal bore of the tubing T to the etched channel 210E. In general it is important to insure that the fluid communication between the tube T, coupler 204B, and interface surface 210F can be made gas tight by crimping the coupler 204B on the tube T and brazing or crimping the interface surface 204F onto the prepared interface surface 210F. Alternately, the braze could be omitted and the interface surfaces may be prepared with a ductile surface material, or a high temperature ceramic cement, such that crimping alone is sufficient to provide a gas-tight seal. Sufficient overlap of the two interface surfaces 210F and 204F allow the location of the brazing or cement to be distanced if necessary from the opening of the etched channel 210E. Capillary action would keep the braze material in the confined spaces between the closely fitting parts and away from the exposed entrance to the etched channel 210E. Alternately, the fitting may be fabricated to have flaps or tabs (not shown) which could be spot welded into place, or could be attached by crimping to form a gas tight seal. In still another embodiment, the receiving bore 204R can be threaded to engage a threaded fitting (not shown) that may be supplied on the end of the tube T.

In another feature of the present invention, illustrated in FIGS. 3A–3B, the preferred embodiment 200 of the planar chromatographic assembly 120 also includes means for effecting a controlled temperature of the separation column 205. As shown in FIG. 3A, when the preferred embodiment 200 is operated in a first mode, the intake and exhaust shutters 240, 241 are located in their closed positions, whereby operation of the fan 220 by the fan motor 222 causes closed-circuit recirculation of air in the oven cavity through intake port 244 and exhaust port 245 and the respective heating cartridges 248. Such operation of the fan 220 and controlled application of heat via the heating cartridges 248 allow for separations of a sample compound according to a controlled oven temperature profile. Rapid cooling of the oven cavity is illustrated in FIG. 3B, wherein the preferred embodiment 200 is shown in a second mode, with the intake and exhaust shutters 240, 241 are located in open positions, whereby operation of the fan 220 by the fan motor 222 causes flow-through circulation of ambient air through the oven cavity via a cover intake vent 229V, intake ports 243, 244, recess 240R, exhaust ports 246, 247, recess 241 R, and cover exhaust vent 229V. During this second mode the respective heating cartridges 248 are inactive. A third mode of operation is contemplated, wherein the intake and exhaust shutters 240, 241 are both located between their open and closed positions such that ambient air may be mixed and circulated within the oven cavity. As will be appreciated by the cross-sectional view of FIG. 3A, the fan motor 222 and associated bearings are used to support the spinning shaft 221 of the fan 220. The fan motor 222 is thus rigidly mounted in the cover 228 yet insulated from the temperature extremes of the oven cavity.

Figure 5:
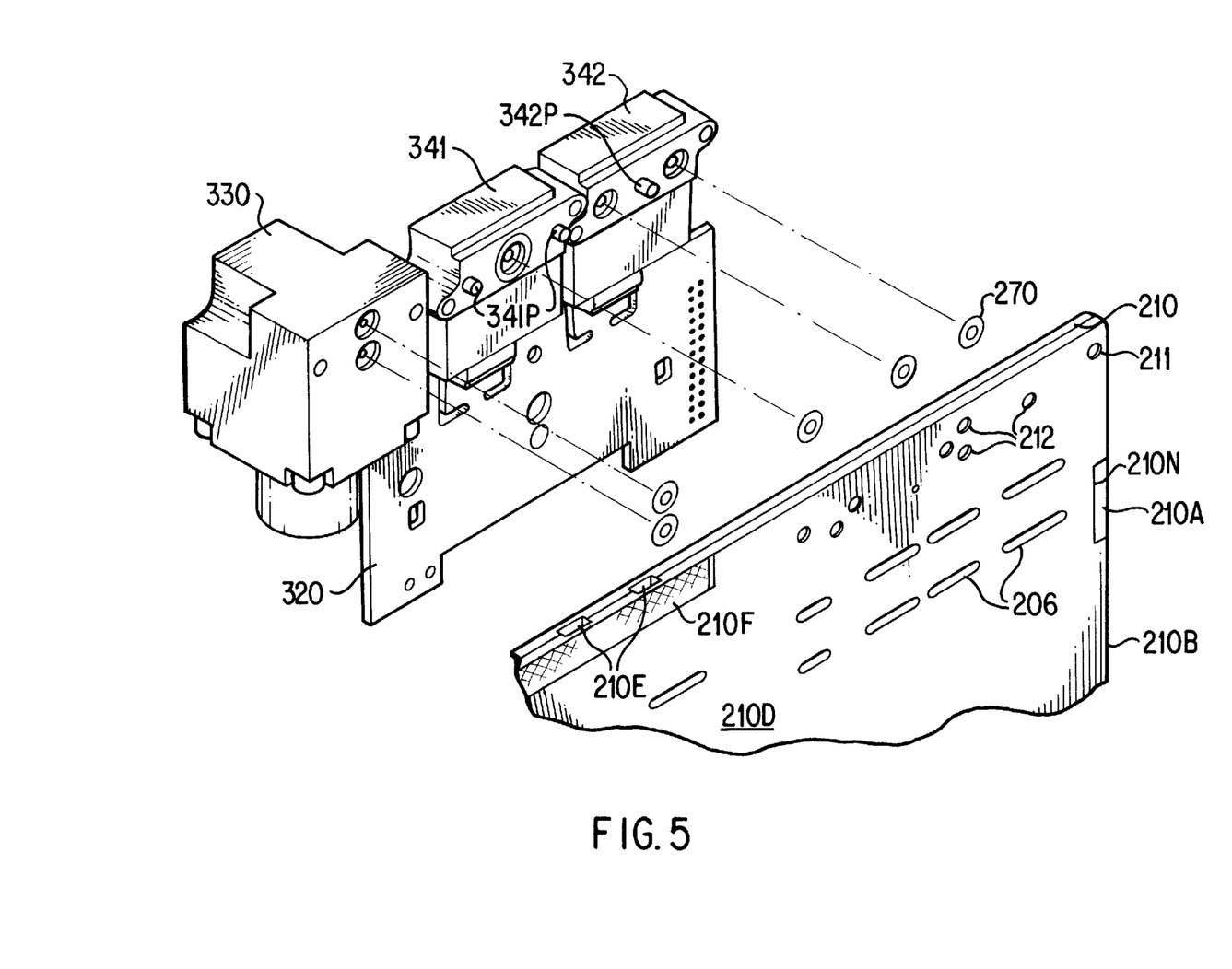
FIG. 5 is side perspective view of a first exploded portion of a planar manifold wherein certain surface-mounted components of the planar manifold being common to one side of the planar manifold are illustrated for clarity.
Figure 6:
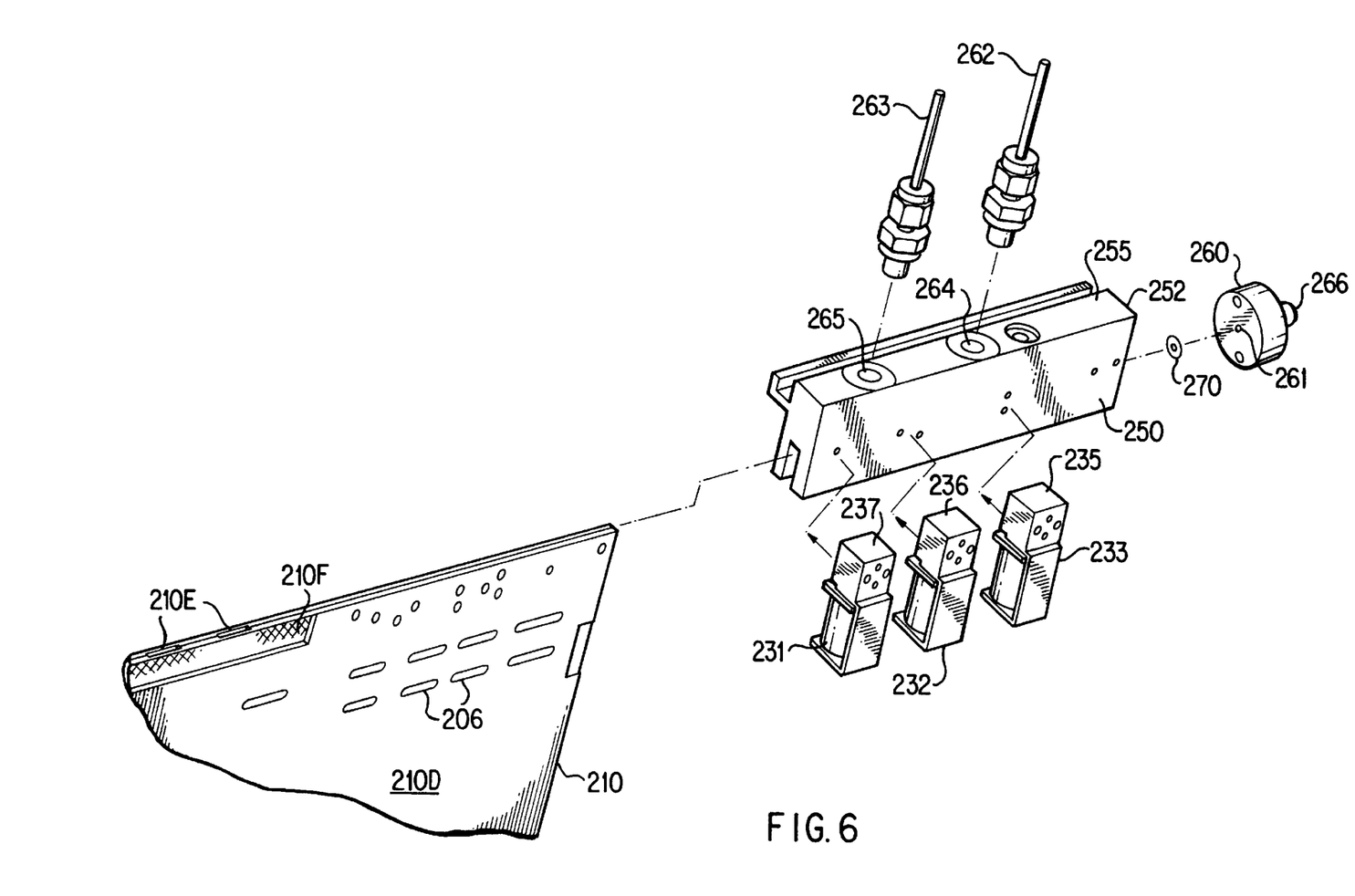
FIG. 6 is side perspective view of a second exploded portion of the planar manifold wherein certain edge-mounted components of the planar manifold assembly being common to one edge of the planar manifold are illustrated for clarity.

As shown in FIGS. 4–6, alternative arrangements may be accomplished for surface-mounting and edge-mounting certain fluid-handling functional devices. For example, valve 231 may be constructed as a surface mount solenoid valve; the second valve 232 and the third valve 233 are each constructed as surface mount proportional valves; a flow controller 330 may be constructed as a purge flow controller; and a first sensor 341 may be constructed as a pressure sensor and a second sensor 342 may be constructed as a flow sensor. Further, a supply fitting 260 may be constructed to receive carrier gas from a supply line (not shown) at a supply line fitting 266. The supply fitting 260 attaches to a first lateral port surface 252 in the fitting block 250 so as to transfer a flow of carrier gas from a through hole 261 into a port (not shown) in the edge mating surface 251 in a fitting block 250. The supply fitting may also includes an internal fit (not shown). That is, the fitting block 250 is constructed to include a plurality of internal, fluid-bearing passageways that are connected to at respective ports on the inner edge mating surfaces 251 of the fitting block 250.

As illustrated in FIG. 5, each port on a surface-mounted fluid-handling functional device (such as purge flow controller 330, first sensor 341, and a second sensor 342) is recessed to allow use of O-rings 270 for face-sealing the device to the planar manifold 210. For example, one or more of the mounting blocks 235, 236, 237 in the fluid-handling functional devices may be face sealed to the fitting block 250. The respective valve block faces 237, 236, 235 of first valve 231, second valve 232, and third valve 233 may be clamped to the fitting block 250 and are thus face-sealed to the planar manifold 210 by suitable means known in the art, such as fasteners (not shown). A carrier gas line 262, and a detector gas line 263 are also connectable via conventional fittings to the fitting block 250. The fitting block 250 may be secured and sealed to the planar manifold 250 by conventional means such as o-rings and fasteners that pass through the fitting block 250 and appropriate throughholes in the planar manifold 210, so as to be secured. However, in a particular feature of the present invention, the mating surfaces 251 may be constructed for crimp fitting on a prepared edge interface surface 210F of the planar manifold 210. Recesses or through holes in the edge interface surface 210F aid in aligning the fitting block 250 with the edge-wise openings 210E of certain internal conduits. With the use of brazing or adhesive, the longitudinal port surface 251 of the fitting block 250 is clamped or crimped onto the planar manifold 210 by way of suitable means (not shown).

A notch 210N in the rear plate 210B is included at manufacture to correspond with one of several indicia inscribed on the front plate 210A so as to define a particular pneumatic configuration that is served by the planar manifold 210. In the illustrated embodiment, the notch 210N may indicate by its location that the planar manifold 210 is intended for use in a split/splitless (S/SL) inlet configuration. Upon modifications to the back plate 210B, there are contemplated other preferred embodiments of the planar manifold 210 that are designed for use in other inlet configurations. For example, a typical split-splitless injection port requires at least three different interconnected flow paths. One is a source of gas, another is a septum purge flow path, and a third is the split vent line. The inlet section 203 may also have several other details such as a particular connection to the separation column 205, or a particular installation of the injection port liner with several seals, and the interface for a septum holder to the inlet section. It is a feature of the present invention that the construction of one of the front plate 210A and back plate 210B may be made common to all of the contemplated configurations, and that the back plate 210B will vary in its construction according to the type of configuration that is to be served. This feature thus makes the front plate 210A a more versatile piece part, thus lowering the parts count and reducing manufacturing costs. In addition, the location of the notch 210N can be sensed during assembly of the planar chromatographic assembly 120 to ensure that the planar manifold 210 has been properly configured for the particular inlet configuration.

The planar manifold 210 can include a variety of other physical features for accommodating certain mechanical functions, such as to accommodate a connector or cabling for one or more data and control signal interface boards 320. Stand-offs consisting of simple posts may be mounted to the portions of the planar manifold 210 on which the separation column 205 is positioned. Oblong openings 206 are distributed longitudinally to effect a thermal break between the perimeter of the planar manifold 210 and the interior portions where the heating element cartridges 248 are located. These thermal breaks impede the transfer of heat from the interior of the planar manifold 210 to the exposed portions, e.g. in the vicinity of the pneumatics section 202, etc. Thermal breaks can also be located so as to effect a degree of localized heating in certain portions of the planar manifold 210 (such as the portion which underlies the inlet section 203 and detector section 207). Alternatively, the planar manifold 210 can include integral resistive heaters or catalytic fuel heaters (not shown) to selectively supply heat to such localized heating zones. (Catalytic fuel heating is described in commonly-assigned, copending U.S. patent application Ser. No. 08/320486, filed on Oct. 11, 1994 in the names of Berger et al., the disclosure of which is included herein by reference.) Locator holes are provided for locating and aligning components within the preferred embodiment 200; for example, as corner holes 211 are provided for locating the planar manifold 210 on respective protrusions (not shown) on the insulating covers 228, 229; through-holes 212 allow passage of the protrusions 341P, 342P used to locate sensors 341, 342 onto to the planar manifold 210, and so on. Additional structural elements may be welded, bolted or otherwise attached to the planar manifold 210.

It will be recognized that the planar chromatographic assembly illustrated in FIG. 1 as a system of functional blocks, and in FIGS. 2–6 having certain components omitted for clarity. However, the planar chromatographic assembly 120 is contemplated as including, as may be necessary and as known in the art, other components in addition to those illustrated and described herein, such as wiring harnesses, additional electrical connectors, mounting or assembly hardware, and other components necessary or complementary to the functions described above.

The advantages of the planar chromatographic assembly 200 of the present invention include: the abovementioned compact, low-profile form factor; the reduction of external connections between fluid-handling functional devices (such as fittings, valves, sensors, and the like) by use of a single planar manifold for the provision of structural support member that has integrated therein a plurality of flow paths; use of the fluid-handling functional devices that connect to the planar manifold, which can advantageously be constructed to be either edge-mounted or surface-mounted, which will allow a very compact, low-profile assembly and yet also offer reliable, fluid-tight connection without the complexity and difficulty of conventional pneumatic connections; the number and complexity of external connections, which would otherwise undesirably increase the overall volume of the planar chromatographic assembly, are also decreased.

A further advantage of the present invention is that a plurality of fluid-handling functional devices may be assembled in a smaller volume at a lower manufacturing cost than is possible in prior art systems. This results from use of the etched channels that are integrated in the planar manifold, and thus many of the fluid flow paths are now integral to the planar manifold, which is itself quite compact and amenable to construction in a variety of shapes and configurations. For example, it is contemplated that the planar manifold and the associated components such as the insulating enclosures may be constructed, if necessary, in a curved, bent, or angled configuration, so as to conform to an irregularly-shaped, compact volume.

A large number of fluid-handling functional paths may thus be integrated into a compact, low-profile form factor in a fashion that heretofore would be difficult if not impossible to assemble using traditional tubular pipe, ferrules, and manual fittings. Also, considerable cost savings and improved reliability are realized by reduction of the number of connections necessary to achieve multiple flow paths.

The surface-mounted pneumatic connections provided by the invention also reduce the complexity of the planar chromatographic assembly, which is desirable during the stages of manufacturing, assembly, repair, or modification of the analytical instrument in which the planar manifold assembly may be situated.

Another advantage is that the planar chromatographic assembly is constructed to use a conventional separation column, thus saving cost and providing ease of use.

Another advantage is that the oven cavity may be significantly reduced in volume in comparison to prior art chromatographic systems, yet the tasks of accessing the oven cavity and mounting or replacing a conventional separation column located therein are met with ease. The oven cavity, being more compact, may be heated more efficiently and thus the planar chromatographic assembly consumes less operating power. The contemplated oven is expected to consume in the range of 100–300 watts of power, and preferably less; oven temperature is expected to be in the range of 50 to 250 degrees centigrade; although these ranges may differ depending upon the application and the insulating quality of the insulating enclosures.

While the invention has been described and illustrated with reference to specific embodiments, those skilled in the art will recognize that modification and variations may be made without departing from the principles of the invention as described herein above and set forth in the following claims.

What is claimed is:

1. A chromatograph, comprising:
    a planar chromatographic assembly including :
        a planar pneumatic manifold having a plurality of internal channels capable of fluid flow;
        a temperature control assembly for establishing a temperature-controlled zone;
        an enclosure for confining the temperature-controlled zone to a space that is adjacent a major surface of the planar pneumatic manifold;
        a separation column having inlet and outlet ends connected in fluid-tight communication with respective ones of the internal channels; wherein the separation column is located adjacent said major surface and within the temperature-controlled zone;
    wherein the planar manifold assembly further comprises an inlet section integrated in an edge of the planar manifold and wherein the planar chromatographic assembly has a compact, low-profile form factor.

2. The chromatograph of claim 1, further comprising a fluid-handling functional device mounted to the planar pneumatic manifold and wherein the fluid-handling functional device is selected from the group consisting of: a) passive devices; b) active devices operable in response to a control signal from the control system for controlling fluid flow in one or more selected etched channels in the planar manifold, and c) signal generating devices operable so as to provide a detection signal indicative of a characteristic of the fluid flow in the separation column.

3. The chromatograph of claim 2, further comprising a fluid-handling functional device mounted to the planar pneumatic manifold and wherein at least one of the inlet and outlet ends are connected to the respective ones of the internal channels by way of the fluid-handling functional device.

4. The chromatograph of claim 3 wherein the fluid-handling functional device is edge-mounted to the planar pneumatic manifold.

5. The chromatograph of claim 2, wherein the planar manifold includes:
   a front plate having a front surface, a back plate having a back surface, and wherein the planar manifold includes an edge surface,
   a selected one of said channels communicating with one of said front surface, back surface, and edge surface; and the fluid-handling functional device having at least one port thereon being connected to said selected one of said channels at one of the front surface, back surface, and edge surface so as to achieve fluid communication with the selected one of said channels.

6. The chromatograph of claim 1, wherein the inlet section has integrated therein a liner situated within a channel in the planar manifold, wherein the liner provides fluid communication with an injection port on the edge of the planar manifold.

7. A chromatograph, comprising:
   a planar chromatographic assembly including:
      a planar pneumatic manifold having a plurality of internal channels capable of fluid flow;
      a temperature control assembly for establishing a temperature-controlled zone;
      an enclosure for confining the temperature-controlled zone to a space that is adjacent a major surface of the planar pneumatic manifold;
      a separation column having inlet and outlet ends connected in fluid-tight communication with respective ones of the internal channels; wherein the separation column is located adjacent said major surface and within the temperature-controlled zone;
   wherein the planar manifold assembly further comprises an inlet section integrated in an edge of the planar manifold and wherein the planar chromatographic assembly has a compact, low-profile form factor,
   wherein the temperature controlled zone further comprises an oven cavity and the temperature control assembly further comprises:
      an intake port and an exhaust port;
      a fan; and
      a shutter assembly mounted to the planar manifold, including an intake shutter, an exhaust shutter, and a shutter motor for moving said intake shutter and said exhaust shutter; wherein the intake shutter is selectably positionable with respect to the intake port and the exhaust shutter is selectably positionable with respect to exhaust port, said intake and exhaust ports being located with respect to the fan and the oven cavity for respectively permitting intake and exhaust air flow therethrough;
   wherein at least one of the intake port and exhaust port include a heating element cartridge that may be selectively actuated to heat the air moved by the fan through the shutter assembly for heating the oven cavity.

8. The chromatograph of claim 7, wherein the fan includes a fan blade assembly and the separation column and the fan blade assembly are respectively mounted on opposite upper and lower major surfaces of the planar manifold and adjacent a flow-through section between said upper and lower major surfaces, such that heated air may be exchanged through the flow-through section of the planar manifold.

9. The chromatograph of claim 1, wherein the separation column is attached to the major surface and located in parallel with the major surface so as to thereby reduce the overall thickness of the planar chromatographic assembly.

* * * * *